United States Patent
Andersson et al.

(10) Patent No.: US 11,981,887 B2
(45) Date of Patent: *May 14, 2024

(54) BIOREACTOR INCLUDING A ROCKING DEVICE

(71) Applicant: Cytiva Sweden AB, Uppsala (SE)

(72) Inventors: Andreas Andersson, Uppsala (SE); Lars Johan Carlsson, Kungsangen (SE); Christian Elnegard, Saltjo-Boo (SE); Henrik K. Eriksson, Uppsala (SE); Thomas Falkman, Uppsala (SE); Patric Fricking, Uppsala (SE); Linnea Troeng, Uppsala (SE); Claes Peterson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/174,322

(22) Filed: Feb. 24, 2023

(65) Prior Publication Data

US 2023/0212497 A1    Jul. 6, 2023

Related U.S. Application Data

(63) Continuation of application No. 15/653,501, filed on Jul. 18, 2017, now Pat. No. 11,613,726, which is a
(Continued)

(30) Foreign Application Priority Data

Feb. 23, 2011   (SE) .................................. 1150154-1

(51) Int. Cl.
*C12M 1/00*   (2006.01)
*B01F 31/23*  (2022.01)
(Continued)

(52) U.S. Cl.
CPC ............. *C12M 27/16* (2013.01); *B01F 31/23* (2022.01); *B01F 35/513* (2022.01); *C12M 23/14* (2013.01); *C12M 23/50* (2013.01)

(58) Field of Classification Search
CPC ....... B01F 31/23; B01F 35/513; C12M 23/14; C12M 23/50; C12M 27/16
(Continued)

(56) References Cited

U.S. PATENT DOCUMENTS

| 3,735,964 A | 5/1973 | Lorenzen |
| 5,057,429 A | 10/1991 | Watanabe et al. |

(Continued)

FOREIGN PATENT DOCUMENTS

| CN | 2468896 Y | 1/2002 |
| CN | 200977885 Y | 11/2007 |

(Continued)

OTHER PUBLICATIONS

Chinese Office Action for CN Application No. 201910891788.2 dated Aug. 15, 2022 (14 pages).
(Continued)

*Primary Examiner* — Lydia Edwards
(74) *Attorney, Agent, or Firm* — Eversheds Sutherland (US) LLP

(57) ABSTRACT

The present invention relates to a bioreactor including at least one reactor vessel in form of a plastic bag, a tray (4) for holding said at least one bag, a rocking device for limited rocking motions of the tray (4) around a rocking axis (2). According to the invention the bioreactor comprises a device (6,7,8,9) for enabling swinging of the tray (4) around a second axis (7) parallel to and distanced from the rocking axis (2).

10 Claims, 2 Drawing Sheets

Related U.S. Application Data continuation of application No. 13/984,887, filed as application No. PCT/SE2012/050187 on Feb. 21, 2012, now Pat. No. 9,738,863.

(51) Int. Cl.
*B01F 35/513* (2022.01)
*C12M 3/06* (2006.01)

(58) Field of Classification Search
USPC ....................................................... 435/289.1
See application file for complete search history.

(56) References Cited

U.S. PATENT DOCUMENTS

| | | | |
|---|---|---|---|
| 5,071,760 | A | 12/1991 | Watanabe et al. |
| 6,190,913 | B1 | 2/2001 | Singh |
| 7,195,394 | B2 | 3/2007 | Singh |
| 2005/0186669 | A1 | 8/2005 | Ho et al. |
| 2008/0160597 | A1 | 7/2008 | Van Der Heiden et al. |
| 2009/0019777 | A1 | 1/2009 | Flesch et al. |
| 2010/0129899 | A1 | 5/2010 | Oosterhuis |
| 2010/0144022 | A1 | 6/2010 | Surapaneni |
| 2010/0201167 | A1 | 8/2010 | Wieclawski |
| 2013/0316446 | A1 | 11/2013 | Andersson et al. |

FOREIGN PATENT DOCUMENTS

| | | |
|---|---|---|
| EP | 1739165 A1 | 1/2007 |
| EP | 2678416 A1 | 1/2014 |
| GB | 2411178 A | 8/2005 |
| JP | 62-289175 A | 12/1987 |
| JP | 2001-055146 A | 2/2001 |
| JP | 2011-078386 A1 | 4/2011 |
| WO | 2000/066706 A1 | 11/2000 |
| WO | 2012/115581 A1 | 8/2012 |

OTHER PUBLICATIONS

Non-Final Office Action Received for U.S. Appl. No. 13/984,887, dated Apr. 13, 2015, 11 pages.
Final Office Action Received for U.S. Appl. No. 13/984,887, dated Oct. 29, 2015, 11 pages.
Non-Final Office Action Received for U.S. Appl. No. 13/984,887, dated May 9, 2016, 12 pages.
Final Office Action Received for U.S. Appl. No. 13/984,887, dated Nov. 3, 2016, 13 pages.
Non-Final Office Action Received for U.S. Appl. No. 13/984,887, dated Jan. 18, 2017, 11 pages.
Notice of Allowance Received for U.S. Appl. No. 13/984,887, dated Apr. 19, 2017, 7 pages.
Office Action Received for Chinese Patent Application No. CN201280009949.7, dated Jun. 20, 2014.
Office Action Received for Chinese Patent Application No. CN201280009949.7, dated Mar. 28, 2016.
Supplemental Search Report Received for European Patent Application No. 12749410.2, dated May 9, 2016, 4 pages.
International Preliminary Report on Patentability Received for PCT Patent Application No. PCT/SE2012/050187, dated Sep. 6, 2013, 6 Pages.
International Search Report and Written Opinion Received for PCT Patent Application No. PCT/SE2012/050187, dated Apr. 16, 2012, 8 Pages.
Taitec, "Angle rack for test tubes:AT-1250", available online at<http://e-taitec.com/products/products-detail-en.php?machine_name=AT-1250>.

BIOREACTOR INCLUDING A ROCKING DEVICE

CROSS REFERENCE TO RELATED APPLICATIONS

This application is a continuation of U.S. application Ser. No. 15/653,501, filed Jul. 18, 2017, which is a continuation of U.S. application Ser. No. 13/984,887, filed Aug. 12, 2013, which claims the priority benefit of PCT/EP2012/050187 filed on Feb. 21, 2012, which claims priority benefit of Swedish Patent Application No. 1150154-1 filed on Feb. 23, 2011, the entire contents of which are incorporated herein by reference.

TECHNICAL FIELD

The present invention relates to a bioreactor including at least one reactor vessel in form of a plastic bag, a tray for holding said at least one bag, a rocking device for limited rocking motions of the tray around a rocking axis.

BACKGROUND TO THE INVENTION

Bioreactors of the above mentioned type are for example manufactured by GE Healthcare, Uppsala, Sweden under the trade name WAVE Bioreactor™ in several variants for different sizes of reactor bags. Other bioreactors of this type are also known. In reactors of this type, bags containing cell culture medium is placed on a tray which in turn is attached to a rocking device. The rocking motion of this device induces waves in the cell culture medium. These waves provide mixing and oxygen transfer, resulting in a perfect environment for cell growth.

The bags are clamped at two ends to the tray which for this purpose contains clamping devices, Bioreactors of moderate sizes are often placed on benches in laboratories and the like. If the bench is not accessible from two sides, the person who is to take off a used bag or placing a new bag on the tray must then lean over the bioreactor to reach the clamp on one side of the tray. Such leaning is not suitable from an ergonomic point of view and for shorter persons it can even be hard to reach the clamp in question.

Depending on the size of the bag or bags to be placed on a tray, different sizes of trays are used in the same bioreactor. For a bench placed bioreactor the means for fixing the tray to the rocking device are on one side hidden from view by the tray itself which WO 00/66706 discloses a bioreactor of the above mentioned type, in which the tray can be swung up to a vertical position around a centre axis in order to obtain stratification of the mixture in the reactor vessel.

The objective of the present invention is to improve bioreactors of the above mentioned type so that application and changes of plastic bags and the removal and application of trays can be performed in a better way from an ergonomic point of view.

SUMMARY OF THE INVENTION

This objective is accomplished by a bioreactor including at least one reactor vessel in form of a plastic bag, a tray for holding said at least one bag, a rocking device for limited rocking motions of the tray around a rocking axis, characterized by a device for enabling swinging of the tray to an upright position around a second axis parallel to and distanced from the first axis. Thereby, the bioreactor can be placed on a bench so that the tray is pivoted against the front side of the bench, i.e. towards a person who intend to change reactor vessel or tray, whereby such a change can be performed in an acceptable way from an ergonomic point of view. Also a change of tray can be performed in an ergonomic manner. Another advantage by an upright position of the tray is that emptying of fluid in the reactor vessel is assisted by gravity.

In a preferred embodiment, the device for enabling swinging of the tray around a second axis comprises at least one gas spring damper.

The bioreactor comprises in a second embodiment means for releasably locking the tray in set positions.

In the preferred embodiment, the tray is detachably attached to an intermediate plate which is attached to the rocking device by a hinge connection located at a distance from the rocking axis and to which one end of the at least one gas spring damper is pivotally attached. The rocking device comprises preferably a rocking platform to which the intermediate plate is attached by a hinge connection and to which the at least one gas spring damper is pivotally attached.

A yoke can be provided, which in one end is pivotally attached to the intermediate plate, the opposite end of the yoke being insertable into locking means provided on the rocking platform for locking the intermediate plate against downward swinging.

In the preferred embodiments the tray can be pivotable around an axis being perpendicular to the plane of the tray.

BRIEF DESCRIPTION OF THE DRAWING

The invention will now be described with reference to the enclosed figures, of which.

DESCRIPTION OF EMBODIMENTS

Figure 1:
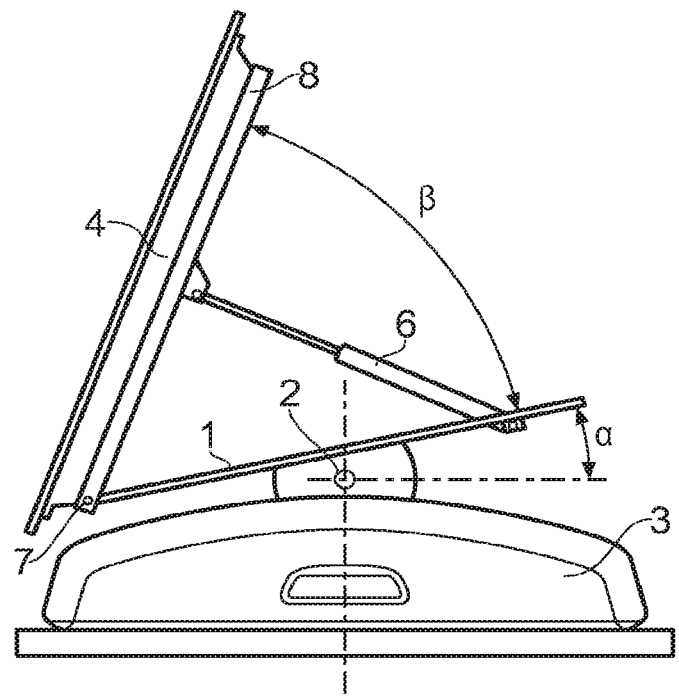
FIG. 1 shows a schematic side view of a bioreactor without reactor vessel according to a first preferred embodiment of the present invention, FIG. 2 schematically shows a perspective view from behind of the bioreactor in FIG. 1 with the tray separated from the intermediate plate, FIG. 3 schematically shows a side view of a bioreactor according to a second preferred embodiment, and FIG. 4 schematically shows a perspective view from the front side of a bioreactor according to a third preferred embodiment.

The different embodiments ill figures in FIGS. 1-4 are all based on a bioreactor manufactured by GE Healthcare, Uppsala, Sweden under the trade name WAVE Bioreactor™. Such a bioreactor comprises a rocking platform 1 and a mechanism for pivoting platform 1 back and forth around a rocking axis 2. This mechanism and means for controlling the rocking mechanism are located in a housing 3. During rocking movements of the platform 1, the platform forms an angle α to the horizontal in the end of the upward movement thereof. Thus, the rear end of the platform moves back and forth from an angle of −α to +α. The construction of such a bioreactor is well known to persons skilled in the art and need not be further described in order to enable an understanding of the present invention.

In the known version of said bioreactors, a tray 4 is releasably attached to the platform 1. The reactor vessels in forms of plastic bags (not shown in the figures) are clamped to the tray 4 with the aid of clamping devices 5 (see FIGS. 2 and 4). The angle α is only about 12°, which means that a person who is to take off a used bag or placing a new bag on the tray 4, when this is in alignment with the rocking platform 1, must lean over the bioreactor to reach the clamp on the rear side of the tray (to the right in the figures) if the reactor is placed on a bench. Such leaning is not suitable from an ergonomic point of view and for shorter persons it can even be hard to reach the clamping device in question.

Depending on the size of the bag or bags to be placed on a tray, different sizes of trays 4 are used in the same bioreactor. For a bioreactor placed on a bench the means for fixing the tray 4 to the rocking platform 1 are on one side hidden from view by the tray itself which makes the changing of trays troublesome and time consuming. Furthermore, the lifting off a tray from the rocking platform and the placing of a new tray onto the rocking platform can not be performed in suitable way from an ergonomic point of view.

In order to enable handling in an ergonomic manner of reactor vessels in the form of plastic bags clamped to the tray 4, a bioreactor according to the present invention includes means for placing the tray in an upright position. In the embodiments shown in the figures, the means for placing the tray 4 in an upright position are a pair of gas spring dampers 6, which in the figures are shown in a fully extended state and which pivot the tray 4 around a second axis 7. In FIG. 1, the angle β, i.e. the angle with which the tray swings up from the rocking platform 1, is about 60°. The tray 4 forms thus in FIGS. 1 and 2 an angle α+β=about 72° to the horizontal. In such a position of the tray 4, the clamping devices 5 on both the front side and the rear side of the tray are easily accessible to a person who shall remove a used plastic bag and/or replace it with a new plastic bag. Furthermore, it is easier to empty a plastic bag on the tray in the upright position thereof than in a position when the tray is in alignment with the rocking platform 1 due to the greater influence of gravity in the upright position of the tray. Also the working position for a person who shall change tray is acceptable from an ergonomic point of view when the tray is placed in its upright position. In the upright position the angle α+β lies preferably between 60-90°.

Figure 2:
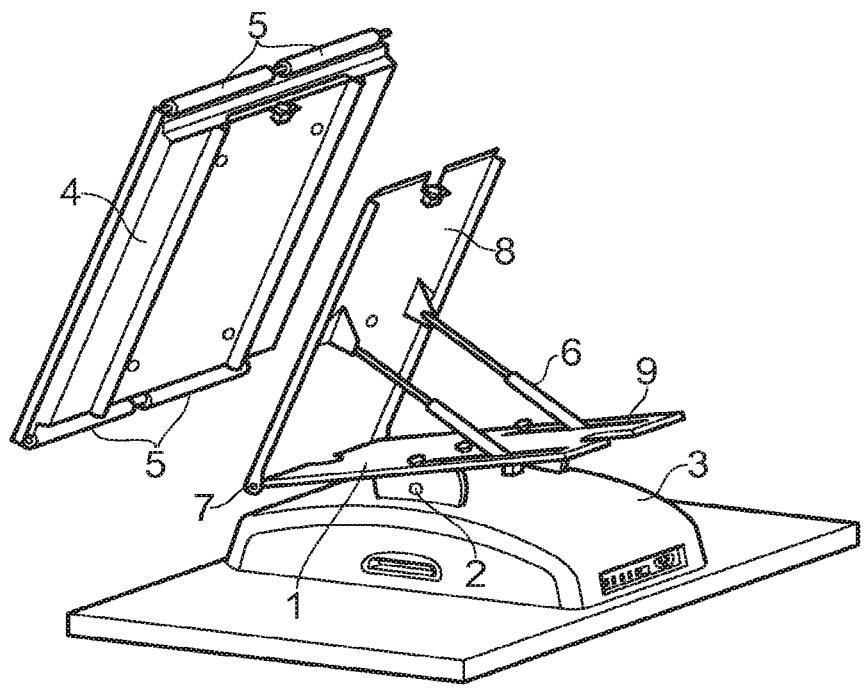
Figure 4:
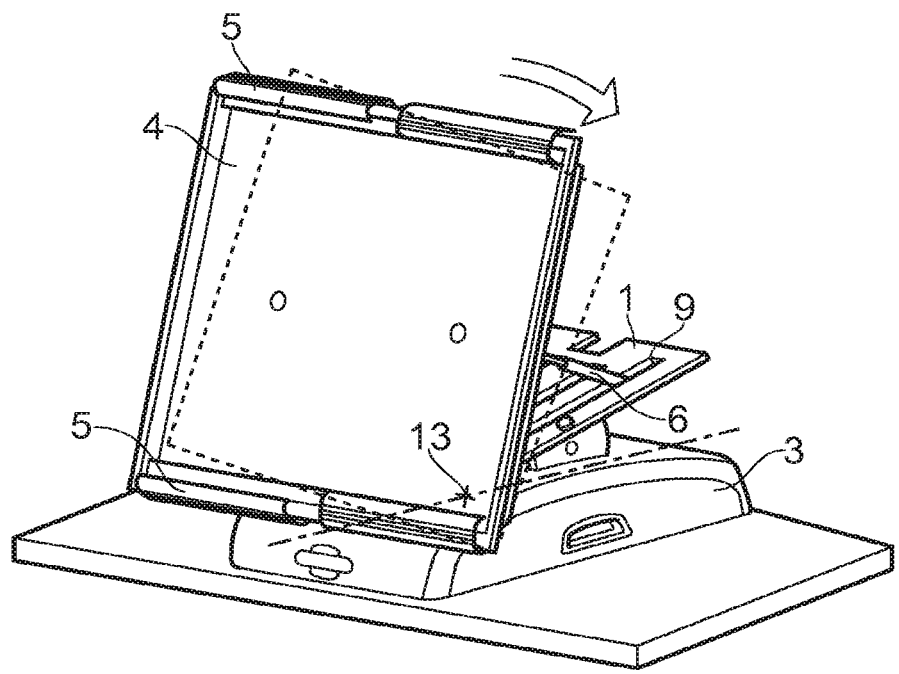

In the embodiments shown, the tray 4 is indirectly attached to the rocking platform 1 via an intermediate plate 8, which carries the pair gas spring dampers 6 and the front end of which is hinged to the front end of the rocking platform 1. As can be seen in FIGS. 2 and 4, the rocking platform 1 has through-going elongate openings 9 for accommodating the gas spring dampers 6 in the downfolded position of the intermediate plate. In the downfolded position of the intermediate plate, the hinged connection of the gas spring dampers to the rocking platform would be located nearer to the plane of the rocking platform than the hinged connection between the gas spring dampers and the intermediate plate. Thereby, the gas spring dampers will in the downfolded position of the intermediate plate act with a force directed away from the intermediate plate and the rocking platform, a so called over-center mounting. In the downfolded position of the intermediate plate, the gas spring dampers thus act to hold together the intermediate plate and the rocking platform. It is first when the intermediate plate has been moved a small distance upwards that the gas spring dampers act to move the intermediate plate to its end position shown in the figures. The force of the gas spring dampers should be such that the tray 4 with full reactor vessels clamped thereto automatically or with the aid of a very small manual force will be moved to the end position shown in FIG. 1.

In order to enable the tray 4 to be replaced by a different tray, the intermediate plate 8 is provided with quick couplings similar to the quick couplings provided on the rocking platform of a WAVE Bioreactor™. It is of course possible to provide trays and intermediate plates with other types of co-operating elements to establish quick couplings.

Figure 3:
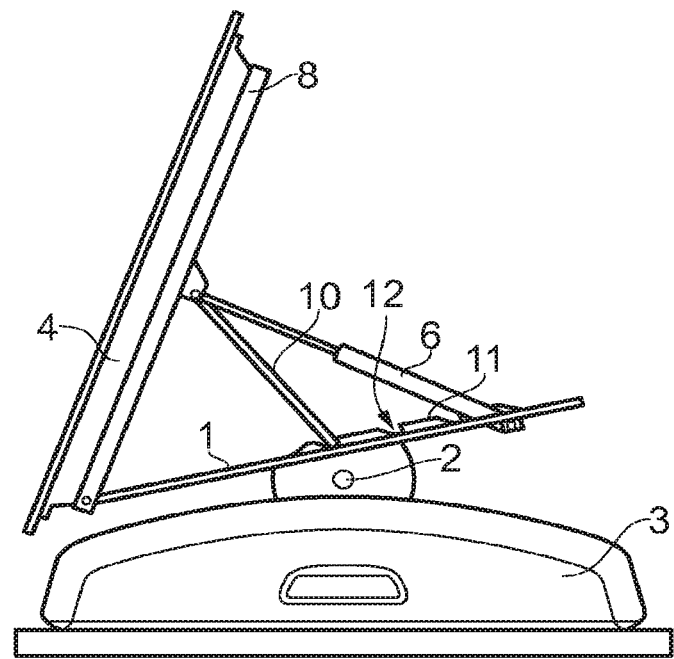

In FIG. 3, a second preferred embodiment is schematically disclosed. This embodiment differs from the embodiment according to FIGS. 1 and 2 only in that means 10-12 for locking the intermediate plate in set positions are present. In all other aspects the bioreactor according to FIG. 3 is similar to the bioreactor described with reference to FIGS. 1 and 2 and identical elements in the bioreactors according to the first and second embodiments are given the same reference numbers. The means for locking the intermediate plate in set positions consist of two upstanding flanges 11 extending in a rearward direction on the rocking plate 1. Each upstanding flange has a row of upwardly open openings 12 extending along the flange. A U-shaped yoke 10 has legs hinged to the intermediate plate and is dimensioned to fit in the openings 12 in the flanges 11. The openings 12 are configured to hold the yoke in the openings against the action of the gas spring dampers 6.

It is possible to dispense with the gas spring dampers in the embodiment according to FIG. 3 and only rely on the locking means 10-12 for holding the tray in an upright position.

In FIG. 4, a third preferred embodiment is schematically disclosed. This embodiment differs from the embodiment described with reference to FIGS. 1 and 2 only in that the tray 4 is attached to the intermediate plate pivotable around a third axis 13 perpendicular to the plane of the intermediate plate. Identical elements according to the first and third embodiments are given the same reference numerals. The pivotable connection forming the third axis 13 could be a pivot arm extending from the intermediate plate into a hole in the tray 4. After releasing the quick coupling and moving the tray 4 out of the plane for the intermediate plate, the tray 4 can be pivoted around axis 13 for example in the direction indicated by an arrow in FIG. 4 to a position indicated by interrupted lines in FIG. 4. In such a position, liquid in a plastic bag attached to the tray 4 will gather in a corner. The possibility to swing the tray 4 around the third axis 13 thus enables a more total emptying of a reactor vessel than in the embodiments according to FIGS. 1-3.

The embodiments shown can be modified in several aspects without leaving the scope of invention. For example, it is not necessary to have to two gas spring dampers, one centrally placed gas spring damper can be enough. Other locking devices than the one shown in FIG. 3 could be used. For example can lockable gas spring dampers be used which enables the user to lock the gas spring dampers in any set position. The gas spring dampers could be connected directly to the tray by easily releasable connections and the tray could then be attached to the front side of the rocking platform by easily releasable connections. Instead of an over-center mounting of gas spring dampers, the intermediate plate can be releasably locked to the rocking platform by a snap connection which is releasable by a mechanism that can be actuated from the front side of the bioreactor. The rocking platform can be eliminated and the rear ends of the gas spring dampers then be attached to other parts of the rocking mechanism. The scope of the patent shall therefore not be limited by the embodiments described but only by the content of the enclosed patent claims.

The invention claimed is:

1. A device for use with a bioreactor, the device comprising:
   a base;

a platform having a first end and a second end and being operably connected to the base, the operable connection providing a rocking motion such that the first and second ends alternately rock up and away from the base;

wherein, the platform first end and the base form a first pivot axis associated with a first angle defined between the base and the platform along the first pivot axis;

a tray being pivotally connected to the platform second end, the pivotal connection forming a second pivot axis associated with a second angle defined between the tray and the platform second end along the second pivot axis; and wherein pivoting of the platform first end about the first pivot axis up and away from the base changes the first angle, and pivoting of the tray about the second pivot axis up and away from the platform changes the second angle, the changes in the first and second angles occurring cooperatively to facilitate extension of the tray from an operating position parallel to the platform to an upright release position.

2. The device of claim 1, further comprising at least one damper longitudinally extending between the platform and the tray, a first end of the at least one damper being coupled to the tray and a second end of the at least one damper being coupled to the platform.

3. The device of claim 2, wherein the damper is a gas spring damper.

4. The device of claim 3, wherein the length of the at least one gas spring damper, a position of the first end of the at least one gas spring damper along the tray, and a position of the second end of the at least one gas spring damper along the platform provides a sum of the first angle and the second angle from 60° to 90° in the upright release position.

5. The device of claim 1, further comprising one of a set of spring dampers for releasably locking the tray in set positions.

6. The device of claim 1, further comprising a hinge connection located at a distance from a first axis and to which one end of at least one gas spring damper is pivotally attached.

7. The device of claim 1, wherein the tray is pivotable around a rotation axis being perpendicular to a plane of the tray.

8. The device of claim 1, further comprising at least one reactor vessel retainably clamped to the tray in the operating position and in the upright release position.

9. The device of claim 1, wherein the second axis further enables the platform first end and the platform second end to pivot between an angle of +alpha and an angle of −alpha with respect to a horizontal line.

10. The device of claim 1, wherein the first axis and second axis together enable the tray to extend upright at an angle of about 72 degrees with respect to a horizontal line.

* * * * *